United States Patent
Brod

(10) Patent No.: US 9,956,268 B2
(45) Date of Patent: May 1, 2018

(54) NEUROPEPTIDE Y TREATMENT OF AUTOIMMUNE DISEASE

(76) Inventor: Staley A. Brod, Bellaire, TX (US)

(*) Notice: Subject to any disclaimer, the term of this patent is extended or adjusted under 35 U.S.C. 154(b) by 0 days. days.

(21) Appl. No.: 13/431,154

(22) Filed: Mar. 27, 2012

(65) Prior Publication Data

US 2013/0259901 A1    Oct. 3, 2013

(51) Int. Cl.
*A61K 38/33* (2006.01)
*A61K 38/22* (2006.01)

(52) U.S. Cl.
CPC .......... *A61K 38/2271* (2013.01); *A61K 38/33* (2013.01)

(58) Field of Classification Search
None
See application file for complete search history.

(56) References Cited

PUBLICATIONS

Bedoui et al., Neuropeptide Y (NPY) Supresses Experimental Autoimmune Encephalomyelitis: NPY1 Receptor-Specific Inhibition of Autoreactive Th1 Responses in Vivo, Oct. 1, 2003, Journal of Immunology 171(7):3451-3458.*
Luhder et al., Small but powereful: Short peptide hormones and their role in autoimmune inflammation, Dec. 10, 2009, Journal of Neuroimmunology 217(1-2):1-7.*
t'Hart et al., Modelling of multiple sclerosis: lessons learned in a non-human primate, Oct. 2004, The Lancet Neurology 3(10):588-597.*
Wekerle et al., Animal models of multiple sclerosis, 2006, Drug Discovery Today: Disease Models 3(4):359-367.*
Behan et al., The sad plight of multiple sclerosis research (low on fact, high on fiction): critical data to support it being a neurocristopathy, Inflammopharmacol 18:265-290, 2010.*
DiBernardo et al., Translating preclinical insights into effective human trials in ALS, 2006, Biochimica et Biophysica Acta 1762: 1139-1149.*
Benatar, M., Lost in translation: Treatment trials in the SOD1 mouse and in human ALS, 2007, Neurobiology of Disease 26: 1-13.*

* cited by examiner

*Primary Examiner* — John D Ulm
(74) *Attorney, Agent, or Firm* — Benjamin Aaron Adler

(57) ABSTRACT

The present invention provides a method for treating or delaying the onset of an autoimmune condition in a human subject comprising orally administering to the subject at an effective dose of neuropeptide Y.

12 Claims, 6 Drawing Sheets

NEUROPEPTIDE Y TREATMENT OF AUTOIMMUNE DISEASE

BACKGROUND OF THE INVENTION

Field of the Invention

The present invention relates generally to the fields of autoimmune diseases. More specifically, the present invention relates to uses of ingested (orally administered) neuropeptide Y.

Description of the Related Art

The following abbreviations may be used herein. ACTH—Adrenocorticotropin hormone, a-MSH—alpha-melanocyte stimulating hormone, CR-EAE—chronic relapsing experimental autoimmune encephalomyelitis, DTH—delayed type hypersensitivity, DPBS—Dulbecco's phosphate buffered saline, neuropeptide Y—NPY, SIRS—soluble immune response suppressor, SPF—specific pathogen free, SST—somatostatin, $T_{reg}$—T regulatory cell.

Experimental autoimmune encephalomyelitis (EAE) is a T cell mediated inflammatory autoimmune process of the CNS that resembles in some aspects the human demyelinating disease multiple sclerosis (MS) (1) and provides a useful animal model for the evaluation of potential therapies for T cell mediated autoimmune diseases (2-4). Ingested immunoactive proteins type I IFN (5), SIRS peptide 1-21 (6), alpha-MSH (7), ACTH (8) and SST (9) inhibit clinical attacks and inflammation in acute experimental autoimmune encephalomyelitis (5, 10).

Ingested immunoactive proteins act by reduction in Th1-like encephalitogenic activity (ingested IFN-α) (6, 7, 10, 11), induction of Th2-like counter-regulatory cytokines (oral SIRS peptide) (6), reduction in CNS Th1-like encephalitogenic cytokines (alpha-MSH) (7), reduction in Th1-like encephalitogenic cytokines IL-2, IFN-γ and IL-17 along with CD4+CD25+ FoxP3+ frequency induction ($T_{reg}$) (ACTH) (8) and reduction of Th1 and Th17 with induction of Th2-like IL-4 cytokines and $T_{reg}$ cells (SST) (9).

Therefore, the prior art is deficient in the use of neuropeptide Y in the treatment of autoimmune diseases. The present invention fulfills this long-standing need and desire in the art.

SUMMARY OF THE INVENTION

The present invention examined whether an immunoactive protein, Neuropeptide Y, would have anti-inflammatory effects in EAE after oral administration. B6 mice were immunized with MOG peptide 35-55 and gavaged with control saline or neuropeptide Y during ongoing disease. Splenocytes from mock fed or neuropeptide Y fed mice were adoptively transferred into active MOG peptide 35-55 immunized recipient mice during ongoing disease. Ingested (oral) neuropeptide Y inhibited ongoing disease, and decreased inflammation. Adoptively transferred cells from neuropeptide Y fed donors protected against actively induced disease and decreased inflammation. In actively fed mice, oral neuropeptide Y decreased Th1-like cytokines and increased Th2-like IL-13 cytokines in both the spleen and the CNS. In recipients of donor cells from neuropeptide Y fed mice there was a reduction of Th1 and Th17 and induction of Th2-like IL-13 cytokines in both the spleen and CNS. Oral neuropeptide Y decreased clinical score and decreased inflammatory foci in both actively fed and recipients of actively fed mice. There was no significant increase in $T_{reg}$ cell frequencies in actively fed or recipients of neuropeptide Y fed donor cells. Thus, ingested (orally administered) neuropeptide Y can inhibit clinical disease, inhibit CNS inflammation by decreasing Th17 and Th1-like cytokines and increasing Th2-like cytokines in the CNS.

The present invention is directed to a method for treating or delaying the onset of an autoimmune condition in a human subject comprising orally administering to the subject an effective dose of neuropeptide Y.

The present invention is further directed to a method of decreasing innate inflammatory cytokines IL-1β and TNF-α, Th1-like cytokines IL-2 and IFN-γ, IL-17 ($T_{eff}$), IL-12p70 and increasing the Th2-like counter-regulatory cytokine IL-13 in a human subject comprising orally administering to the subject an effective dose of neuropeptide Y.

BRIEF DESCRIPTION OF DRAWINGS

The following drawings are part of the present specification and are included to further demonstrate certain aspects of the present invention. The invention may be better understood by reference to the drawings in combination with the detailed description of specific embodiments presented herein.

10 mcg (p<0.03) and increased peripheral splenic lymphocyte production of MOG induced IL-4 (p<0.01), IL-10 (p<0.01) and IL-13 (p<0.05) in neuropeptide Y dosed vs mock dosed mice. This experiment shows a combination of 3 separate experiments (total n=24/group).

Figure 6:
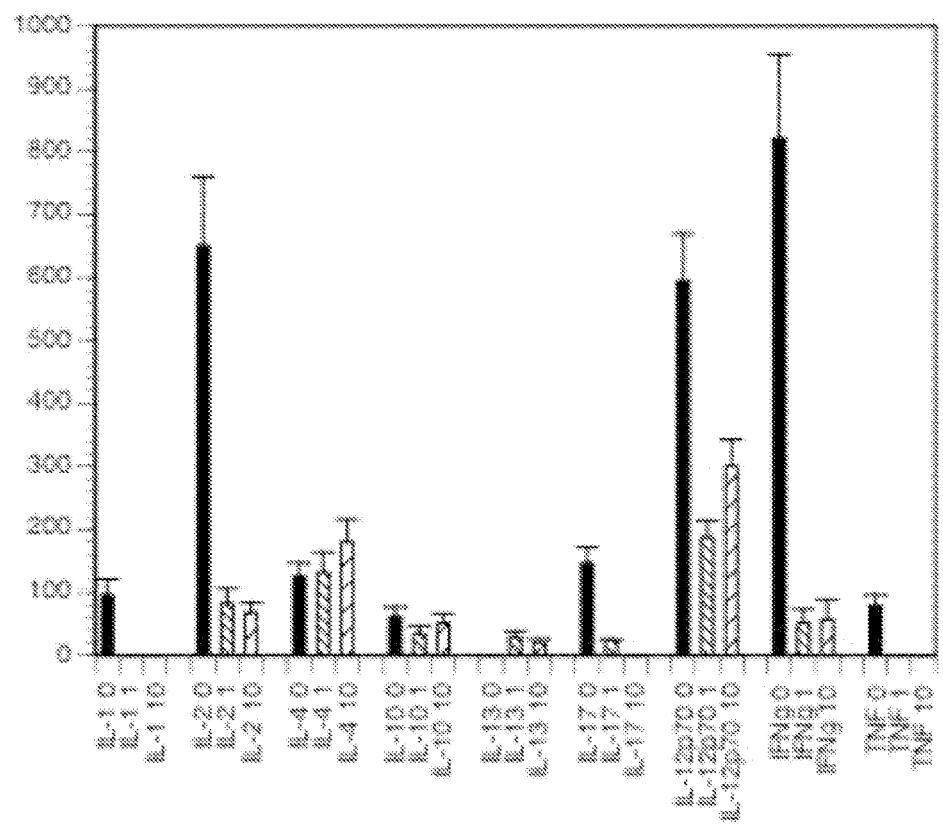

FIG. 6 shows that ingested neuropeptide Y decreases pro-inflammatory and Th-like cytokines in the CNS of actively immunized mice. Lymphocytes isolated from spinal cords from mock fed mice or neuropeptide Y fed mice were stimulated with MOG peptide 35-55 and measured using an inflammatory cytokine antibody array as described in methods. Splenic lymphocytes showed decreased levels of IL-1β (p<0.03), Th1-like cytokines IL-2 (p<0.001), IL-12 (p<0.001), IL-17 (p<0.01), IFN-γ (p<0.001), and TNF-α (p<0.03). Lymphocytes isolated from spinal cords from neuropeptide Y fed mice also showed increased Th2-like IL-13 (P<0.03). This experiment shows a combination of 3 separate experiments (total n=24/group). ND=none detected.

Figure 7:
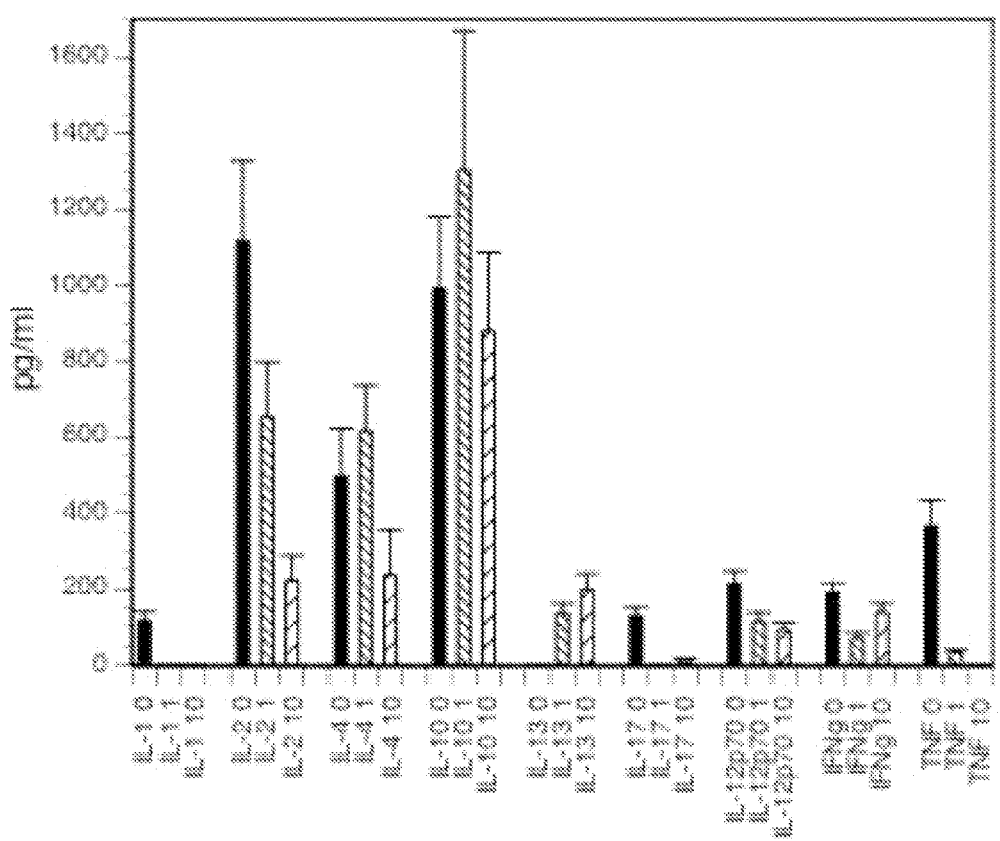

FIG. 7 shows that recipients of donor cells from neuropeptide Y fed mice show decreases in splenic Th1-like cytokines and increased Th2-like IL-13. Whole splenocytes from recipients of mock fed or neuropeptide Y fed donor cells were stimulated with MOG peptide 35-55 and measured using an inflammatory cytokine antibody array as described in methods. Splenic lymphocytes showed decreased levels of IL-1β (p<0.03), Th1-like cytokines IL-2 10 mcg (p<0.001), IL-12 (p<0.05), IL-17 (p<0.03), IFN-γ (p<0.05), and TNF-α (p<0.03) and increased peripheral splenic lymphocyte production of MOG induced IL-13 (p<0.03) in neuropeptide Y dosed vs mock dosed mice. This experiment shows a combination of 3 separate experiments (total n=24/group). ND=none detected.

Figure 8:
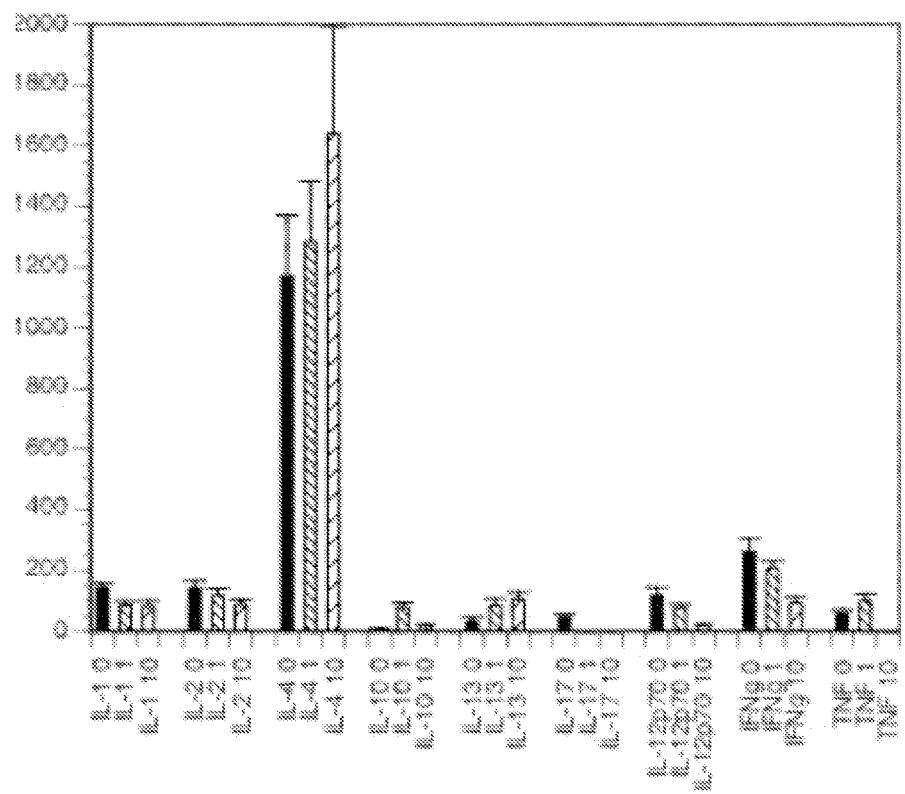

FIG. 8 shows that recipients of donor cells from neuropeptide Y fed mice show decreases in CNS Th1-like cytokines and increased Th2-like IL-10 and IL-13. Lymphocytes isolated from spinal cords from recipients of mock fed or neuropeptide Y fed donor cells were stimulated with MOG peptide 35-55 and measured using an inflammatory cytokine antibody array as described below. CNS lymphocytes showed decreased levels of IL-1β (p<0.05), Th1-like cytokines IL-2 10 mcg (p<0.05), IL-12 (p<0.03), IL-17 (p<0.03), IFN-γ 10 mcg (p<0.03), and TNF-α 10 mcg (p<0.03) and increased peripheral splenic lymphocyte production of MOG induced IL-10 1 mcg (p<0.03) and IL-13 (p<0.03) in neuropeptide Y dosed vs mock dosed mice. This experiment shows a combination of 3 separate experiments (total n=24/group). ND=none detected.

DETAILED DESCRIPTION OF THE INVENTION

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

Treatment of chronic autoimmune disease is challenging even with the advent of new therapeutic techniques. Typical therapies involve the administration of immunosuppressive agents such as steroids. Though steroids are typically not highly effective, they are well tolerated for long term use and many may be administered orally. A non-invasive method for administration, such as oral administration, is highly preferred in cases of chronic diseases such as multiple sclerosis.

In some cases, immunomodulatory polypeptides have also be used for as therapeutics for autoimmune disease treatment. However, methods for administering therapeutic polypeptides typically involve intravenous or subcutaneous injection. For instance, one approved therapy utilizes an injectable porcine ACTH that is administered subcutaneously. Recently, it has been recognized that some polypeptides are biologically active when administered orally. However, previously it was thought that neuropeptide Y would not be active as an oral therapeutic.

The studies described here clearly demonstrate that orally administered and/or ingested neuropeptide Y can be used as a therapeutic treatment for autoimmune disease. The EAE mouse model is a well established model system for the study of human autoimmune disease, more specifically multiple sclerosis. Studies herein show that neuropeptide Y may be orally administered to mice over an extended time period with no detectable toxicity. Furthermore, the oral neuropeptide Y administration significantly reduced clinical symptoms of autoimmune disease as compared to a placebo control in the murine EAE model system. Thus, these studies provide the basis for a new enteral formulations of neuropeptide Y for the treatment of autoimmune disease.

Clinical severity of disease symptoms (e.g. limb weakness, ataxia, and paraplegia) may be evaluated in various ways. In one embodiment of the invention, clinical severity is graded on a numerical scale corresponding to the number or severity of symptoms observed. In a specific embodiment of the invention, clinical symptoms in a murine model are quantified as follows: 0=no disease; 1=minimal or mild hind limb weakness (associated with limp tail); 2=moderate hind limb weakness or mild ataxia (waddling gait and/or poor righting ability); 3=moderate to severe hind limb weakness; 4=severe hind limb weakness or moderate ataxia; 5=paraplegia with no more than moderate four limb weakness; 6=paraplegia with severe four limb weakness or severe ataxia. In another embodiment of the invention, disease symptoms are evaluated by number of inflammatory foci per CNS segment or area. In a very specific embodiment, these evaluations of inflammatory foci are conducted by direct visual observation of the subject CNS post-mortem.

Mitogen stimulation reflects non-antigen and antigen-specific responses, thus the cytokine profiles of stimulated spleen cells or stimulated CNS lymphocytes may also be used to evaluate disease. Stimulation may be provided by NK (natural killer) and T cell stimulant ConA, or MOG peptide 35-55. Thus, in one embodiment of the invention, disease is evaluated by Th1-like cytokines (e.g. IL-2, IFN-gamma, IL12p70, TNF-alpha, IL-1-beta, I-TAC, RANTES), Th2-like cytokines (e.g. IL-4, IL-10, IL-13, CD30, SDF-1, TCA-3) and certain specific cytokines referred to as chemokines (e.g. G-CSF, GM-CSF, MIP-1-.gamma., TECK). Cytokines, including chemokines, that may be profiled to evaluate disease include, but are not limited to: BLC, CD30L, eotaxin, eotaxin-2, FAS ligand, fractalkine, G-CSF, GM-CSF, IFN-gamma, IL-1alpha, IL-1beta, IL-2, IL-3, IL-4, IL-6, IL-9, IL-10, IL-12p40, IL-12p70, IL-13, IL-17, I-TAC, KC, Leptin, LIX, lymphotactin, MCP-1, M-CSF, MIG, MIP-1-alpha, MIP-1-gamma, RANTES, SDF-1, TCA-3, TECK, TIMP-1, TIMP-2, TNF-alpha, sTNF RI, sTNF RII.

The new methods disclosed herein address one of the greatest obstacles to treating chronic disease such autoimmune disease, that is long term tolerance of the therapeutic regimen. Such tolerance takes into account not only biological tolerance, but also tolerance in patients undergoing therapy. Injectable therapeutics are far from ideal for the treatment of chronic disease. Consent injection can result in lasting damage to the tissues around the injection site and is painful and inconvenient for patients. Additionally, injection of any substance into the body increases the risk for infection by bacteria or viruses that may be present in the therapeutic formulations or on the injection apparatus itself. The instant invention enables methods for oral administration of potent immunomodulatory polypeptides. Surprisingly, these polypeptides remain highly active in an oral formulation and are effective for treating autoimmune disease. These new oral therapeutic polypeptides are particularly well adapted for prolonged administration that is often required for the treatment of chronic disease.

Neuropeptide Y compositions according to the instant invention may also be used in conjunction with other therapies that are used for the treatment of inflammation and/or autoimmune diseases. Such secondary therapies can include small molecule drugs as well as therapeutic nucleic acids or polypeptides. Anti-inflammatory agents, for example, are agents that decrease the signs and symptoms of inflammation. A wide variety of anti-inflammatory agents are known to one of skill in the art. Most commonly used are the nonsteroidal anti-inflammatory agents (NSAIDs) which work by inhibiting the production of prostaglandins. Non-limiting examples include, ibuprofen, ketoprofen, piroxicam, naproxen, naproxen sodium, sulindac, aspirin, choline subsalicylate, diflunisal, oxaprozin, diclofenac sodium delayed release, diclofenac potassium immediate release, etodolac, ketorolac, fenoprofen, flurbiprofen, indomethacin, fenamates, meclofenamate, mefenamic acid, nabumetone, oxicam, piroxicam, salsalate, tolmetin, and magnesium salicylate. Another group of anti-inflammatory agents comprise steroid based potent anti-inflammatory agents, for example, the corticosteroids which are exemplified by dexamethason, hydrocortisone, methylprednisolone, prednisone, and triamcinolone as non-limiting examples. Several of these anti-inflammatory agents are available under well known brand names, for example, the NSAIDs comprising ibuprofen include Advil, Motrin IB, Nuprin; NSAIDs comprising acetaminophens include Tylenol; NSAIDs comprising naproxen include Aleve.

As discussed supra, certain known immunomodulatory polypeptides may also be used in accordance with the invention. Such polypeptides include, but are not limited to, SIRS, interferon-alpha and interferon-tau.

Pharmaceutical compositions of the present invention comprise an effective amount of neuropeptide Y and optionally at least one additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains an neuropeptide Y or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, gels (e.g., gelatin), dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

A pharmaceutical composition of the present invention comprising an neuropeptide Y may also comprise different types of carriers depending on whether it is to be administered in solid, liquid or aerosol form, and whether it need to be sterile. The present invention can be administered intranasally, intravitreally, intravaginally, intrarectally, topically, mucosally, intraocularally, orally, topically, locally, via inhalation (e.g. aerosol inhalation), via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a neuropeptide Y composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. In the case of proteinacious compositions of the invention, it may also be preferable that the action of proteases be inhibited during storage of such neuropeptide Y compositions. This can be accomplished by the additional of protease inhibitors and/or the storage of the compositions at low temperature prior to administration.

In embodiments where compositions according to the invention are provided in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In certain embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof an excipient, such as, for example, dicalcium phosphate, mannitol, lactose, starch, magnesium stearate, sodium saccharine, cellulose, magnesium carbonate or combinations thereof a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Methods of the invention will generally be used in an amount of neuropeptide Y effective to achieve the intended purpose. For use to treat or prevent a disease condition, neuropeptide Y, or pharmaceutical compositions thereof, are administered or applied in a therapeutically effective amount. A therapeutically effective amount is an amount effective to ameliorate or prevent the symptoms, or prolong the survival of, the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_5$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

The amount of molecules administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs. In the case of autoimmune disorders, the drugs that may be used in combination with neuropeptide Y of the invention include, but are not limited to, steroid and non-steroid anti-inflammatory agents.

Methods for estimating dose conversions between animal models and humans have previously been developed. In general these algorithms have been used to extrapolate an animal dose to a dose that would be tolerated by a human. For example, method for dose conversions were disclosed by Freireich et al. (1966). The conversion methods taught by Freireich calculate equivalent doses between species using surface area ($m^2$) rather than mass (kg), a method that correlates much more closely to actual data than body mass conversions. Specifically, Freireich teaches how to use an animal 10% lethal dosage ($LD_{10}$) value to estimate the maximum tolerated doses in a human. Freireich also discussed method for converting a dose in mg/kg to a dose in $mg/m^2$ by using the "km" conversion factor for the given animal. For example, in the case of a laboratory mouse the km is approximately 3.0. Thus, in mice $mg/m^2 = k_m$ (3.0 for mice).times.dose in mg/kg.

More recent studies regarding species dose scaling have further elaborated upon the methods of Freireich. These newer studies have reduced error associated with conversion between species to determine human tolerable doses. For example, Watanabe et al. (1992) describes that a conversion of doses between species using body surface area may not be the most accurate method per se for predicting a human equivalent dosage. Nonetheless, the scaling factors set forth by Watanabe yield results that are within the margin of error of the older Freireich conversions. Currently accepted methods for determining a proper starting dose in humans expand upon the methods set forth by Freireich. For example, Mahmood et al. (2003) provides a discussion regarding the choice of a proper starting dose in humans given dose studies in animals.

In additional aspects of the invention neuropeptide Y may be further modified by amino substitutions, for example by substituting an amino acid at one or more positions with an amino acid having a similar hydrophilicity. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Thus such conservative substitution can be made in alpha-MSH and will likely only have minor effects on their activity and in vivo efficacy. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine −0.5); cysteine (−1.0); methionine (−1.3); valine (−1.5); leucine (−1.8); isoleucine (−1.8); tyrosine (2.3); phenylalanine (−2.5); tryptophan (−3.4). These values can be used as a guide and thus substitution of amino acids whose hydrophilicity values are within +2 are preferred, those that are within ±1 are particularly preferred, and those within ±0.5 are even more particularly preferred. Thus, neuropeptide Y may be modified by the substitution of an amino acid, for different, but homologous amino acid with a similar hydrophilicity value. Amino acids with hydrophilicities within ±1.0, or ±0.5 points are considered homologous.

It will also be understood that certain amino acids have specific properties, and thus any amino acid substitution will abolish said property. For example cysteine residues have the unique ability to form di-sulfide bonds that can be crucial for protein structure and activity. Thus, a substitution of cysteine residue for any other amino acid may be expected, by one of skill in the art, to alter the activity of a protein.

Furthermore, neuropeptide Y may comprise one or more modified or unusual amino acid such as 2 Aminoadipic acid, 3 Aminoadipic acid, .beta. alanine, .beta. Amino propionic acid, 2 Aminobutyric acid, 4 Aminobutyric acid, piperidinic acid, 6 Aminocaproic acid, 2 Aminoheptanoic acid, 2 Aminoisobutyric acid, 3 Aminoisobutyric acid, 2 Aminopimelic acid, alpha-methyl leucine, 2,4 Diaminobutyric acid, Desmosine, 2,2' Diaminopimelic acid, 2,3 Diaminopropionic acid, N Ethylglycine, N Ethylasparagine, Hydroxylysine, allo Hydroxylysine, 3 Hydroxyproline, 4 Hydroxyproline, Isodesmosine, allo Isoleucine, Acetylated-lysine, N Methylglycine, sarcosine, N Methylisoleucine, 6 N Methyllysine, N Methylvaline, Norvaline, Norleucine or Ornithine. For example norleucine, a non-templated amino acid that is formed by deamination of lysine, may be substituted at one or more positions. In certain cases, neuropeptide Y compositions of the invention may incorporate amino acids of the "D" chirality that do not naturally occur in proteins, and are thereby resistance to degradation.

In some cases it may be preferable that recombinant neuropeptide Y be fused with additional amino acid sequence. For example, expressed protein may be tagged for purification. Some possible fusion proteins that could be generated include histadine tags, glutathione S-transferase (GST), maltose binding protein (MBP), Flag and myc tagged neuropeptide Y. These additional sequences may be used to aid in purification of the recombinant protein, and in some cases may then be removed by protease cleavage. For example coding sequence for a specific protease cleavage site may be inserted between the neuropeptide Y coding sequence and the purification tag coding sequence. One example for such a sequence is the cleavage site for thrombin. Thus fusion proteins may be cleaved with the protease to free the neuropeptide Y from the purification tag. In further embodiments, recombinant a neuropeptide Y may be further comprise a secretion signal that allow the recombinant protein to be secreted from expressing cells. Thus in some embodiments, neuropeptide Y may be purified from the media of expressing cells.

In certain embodiments it is also contemplated that neuropeptide Y may be chemically synthesized, and purified by methods know to those in the art. For example, rapid, high fidelity methods for peptide and polypeptide synthesis for instance have been described by Miranda & Alewood (1999).

It is an objective of the present invention to demonstrate that oral neuropeptide Y has an anti-inflammatory effect in experimental autoimmune encephalomyelitis in vivo by decreasing Th17, Th1-like cytokines, increasing Th2-like cytokines with $T_{reg}$ induction in the CNS target organ in murine experimental autoimmune encephalomyelitis.

As described in detail below, the present invention is directed to a method for treating or delaying the onset of an autoimmune condition in a human subject comprising orally administering to the subject an effective dose of neuropeptide Y. In one aspect of this method, the neuropeptide Y is administered in a liquid form. In one aspect of this method, the neuropeptide Y is administered in a solid form. Representative examples of condition include but are not limited to rheumatoid arthritis, psoriasis, type 1 diabetes, systemic lupus erythematosus, transplant rejection, autoimmune thyroid disease (Hashimoto's disease), sarcoidosis, scleroderma, granulomatous vasculitis, Crohn's disease, ulcerative colitis, Sjogren's disease, ankylosing spondylitis, polymyositis dermatomyositis, polyarteritis nodosa, immunologically mediated blistering skin diseases, Behcet's syndrome, multiple sclerosis, systemic sclerosis, Goodpasture's disease or immune mediated glomerulonephritis. A person having ordinary skill in this are would be able to prepare satisfactory composition of neuropeptide Y and readily determine appropriate dosages for the condition to be treated. For example, neuropeptide Y may be administered in a dose from about 0.1 mcg to about 50 mg. In one preferred embodiment, neuropeptide Y is administered in a dose from about 1 mg.

In another preferred embodiment, neuropeptide Y is administered in a dose from about 10 mcg. Generally, neuropeptide Y administration decreases levels of IL-1β, IL-2, IL-12p70, IL-13, IL-12, IL-17 ($T_{eff}$), TNF-α and IFN-γ. In addition, neuropeptide Y administration increases levels of IL-4, IL-10 and IL-13. In a preferred embodiment, neuropeptide Y may be administered in combination with a drug such as an anti-inflammatory agent, a SIRS peptide, a-MSH, ACTH and SST.

In another embodiment, the present invention also provides a method of decreasing innate inflammatory cytokines IL-1β and TNF-α, Th1-like cytokines IL-2 and IFN-γ, IL-17 ($T_{eff}$), IL-12p70 and increasing the Th2-like counter-regulatory cytokine IL-13 in a human subject comprising orally administering to the subject an effective dose of neuropeptide Y. In one aspect of this method, the neuropeptide Y is administered in a liquid form. In one aspect of this method, the neuropeptide Y is administered in a solid form. Representative examples of condition include but are not limited to rheumatoid arthritis, psoriasis, type 1 diabetes, systemic lupus erythematosus, transplant rejection, autoimmune thyroid disease (Hashimoto's disease), sarcoidosis, scleroderma, granulomatous vasculitis, Crohn's disease, ulcerative colitis, Sjogren's disease, ankylosing spondylitis, polymyositis dermatomyositis, polyarteritis nodosa, immunologically mediated blistering skin diseases, Behcet's syndrome, multiple sclerosis, systemic sclerosis, Goodpasture's disease or immune mediated glomerulonephritis. A person having ordinary skill in this are would be able to prepare satisfactory composition of neuropeptide Y and readily determine appropriate dosages for the condition to be treated. For example, neuropeptide Y may be administered in a dose from about 0.1 to about 50 mg. For example, in a dose of 10 mcg to a 20 grm mouse—so 10 mcg/0.02 kg so 500 mcg/kg or in a 50 kg person 500 mcg×50=2,5000 mcg or 25 mg/person. Km: Use surface area to weight ratios (km/m$^2$) from 0.020 kg mouse to 50 kg human, the effective dose=1-10 mcg×0.020 kg (mouse)=50-500 mcg/kg×37 kg/m$^2$=1850-18500 mcg/m$^2$=1.85 mg-18.5 mg. For an adult BSA=1.6. For an adult, 2.96 mg-29.6 mg.

Different Dose Normalization Approach: The human equivalent dose for NPY can be defined by converting the effective oral dose in mice to an oral dose in humans (HED—human equivalent dose) by a normalization approach on g/kg basis of the most effective dose (Brod and Khan, 1996). Therefore, the optimal range of doses of 1-10 mcg/20 g in mouse is equivalent to 50-500 mcg/kg=2500-25000 mcg/50 kg or 2.5-25 mg×0.08=0.20 mg-2.0 mg. This formulation is similar to the Km dose with a safety factor=10, i.e., dividing the dose derived from Km conversion by 10 or 250 mcg.

In one preferred embodiment, neuropeptide Y is administered in a dose from about 1 mg.

In another preferred embodiment, neuropeptide Y is administered in a dose from about 10 mcg. Generally, neuropeptide Y administration decreases levels of IL-1β, IL-2, IL-12p70, IL-13, IL-12, IL-17 ($T_{eff}$), TNF-α and IFN-γ. In addition, neuropeptide Y administration increases levels of IL-4, IL-10 and IL-13. In a preferred embodiment, neuropeptide Y may be administered in combination with a drug such as an anti-inflammatory agent, a SIRS peptide, a-MSH, ACTH and SST.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

EXAMPLE 1

Induction of Active EAE

C57BL/6 6-8 week old females were actively immunized, maintained, handled and surveiled as outlined previously (6). Briefly, C57BL/6 6-8 week old females (Jackson Labs, Bar Harbor, Me.) were actively immunized by subcutaneous injection (s.c.) of 0.2 ml inoculum containing 200 mcg MOG peptide 35-55 (Myelin-Oligodendrocyte Glycoprotein peptide fragment 35-55) in IFA (DifcoLabs, Detroit, Mich.) with 800 mcg *Mycobacterium tuberculosus* hominis H37Ra (MT) on day 0 and 7 following (12), with pertussis toxin (PTx) (List Biologicals) 200 ng i.p. on day 0 and day 2 and followed for evidence of disease. Clinical severity was graded daily as follows by a blinded observer: 0=no disease; 1=minimal or mild hind limb weakness (associated with limp tail); 2=moderate hind limb weakness or mild ataxia (waddling gait and/or poor righting ability); 3=moderate to severe hind limb weakness; 4=severe hind limb weakness or moderate ataxia; 5=paraplegia with no more than moderate four limb weakness; 6=paraplegia with severe four limb weakness or severe ataxia.

EXAMPLE 2

Adoptive Transfer

Thirty days after inoculation and after peak score of clinical attack, all spleens from each treatment group were aseptically removed, single cell suspensions prepared, and red cell lysis performed by adding 2-3 ml sterile water to single cells for 5 seconds, and once the solution became transparent, adding AIM-V media to a 50 ml tube. Splenocytes from grouped saline (mock) fed, 1 μg or 10 μg neuropeptide Y fed mice were re-stimulated with MOG peptide 35-55 at a final concentration of 10 μg/ml for 48 hours in serum free medium (AIM-V medium, Gibco BRL, Grand Island, N.Y.) with $2 \times 10^5$ cells/200 ml in triplicate in 96 well U-bottomed plates in a humidified 5% $CO_2$/95% air incubator at 37° C. Following incubation, cells were collected, washed twice in PBS, and viability determined by standard Trypan blue exclusion. Viable concentrations were adjusted to $10^7$ cells/0.5 ml Dulbecco's PBS immediately prior to i.p. injection into active MOG peptide 35-55 immunized recipient mice during ongoing disease (~day 17 post immunization). Following administration of neuropeptide Y or adoptive transfer, clinical outcome is measured by comparing the difference between group mean active treatment and placebo group scores from day 17-30 post immunization.

EXAMPLE 3

Immuno-Active Protein

Neuropeptide Y (human, rat) was purchased from Ascent Scientific.

EXAMPLE 4

Dosing (Feeding) Regimen

Once non-treated inoculated mice attained a clinical score 1.5-2.0, B6 mice were randomized to one of 3 treatment groups, and gavaged (fed) with 0.1 ml of saline (mock), 1 μg, or 10 μg of neuropeptide Y using a 2.5 cm syringe fitted with a 22-24 gauge ball point needle (Thomas Scientific, Swedesboro, N.J.) as previously described (6).

EXAMPLE 5

Histology

Following sacrifice, spinal cords were removed and immersion fixed in 10% neutral buffered formalin for a minimum of two weeks. After fixation, cords were sectioned in entirety in the horizontal plane at approximately 3 mm intervals and processed to paraffin. Paraffin blocks were sectioned at 6-8 microns, and step sections were stained with hematoxylin and eosin and examined by light microscopy. Cord sections were evaluated independently for foci of inflammation by a blinded observer (SAB), without knowledge of the treatment status of the mice prior to sacrifice. Spinal cord tissue was sampled in an identical fashion for each animal and numbers of inflammatory foci per high-powered field (HPF) (>20 perivascular lymphocytes) in the parenchyma were counted.

EXAMPLE 6

Measurement of Cytokine Secretion

Spleens and spinal cords (CNS) from each treatment group were aseptically removed and single cell suspensions prepared. In spinal cords, whole cords were passed through a cell strainer for CNS lymphocytes (B & D, Franklin Lakes, N.J.) and spun at 600 rpm several times to separate lymphocytes from CNS tissue. Splenocytes and cord lymphocytes from grouped saline fed or 10 mcg NPY fed mice were stimulated with 10 mcg MOG peptide 35-55×48 hours as previously described (5, 6). Murine cytokine responses were examined using a customized RayBio Mouse Cytokine Inflammatory Antibody Array including innate cytokine IL-1β and TNF-α, IL-17 (Teff), Th1-like (IL-2, IFN-γ), Th2-like cytokines (IL-4, IL-10, IL-13) and IL-12p70 using the RayBioantibody array Analysis tool application (RayBiotech, Inc, Norcross, Ga.). Results were grouped from mice fed saline or mice fed with NPY from grouped samples of two separate experiments (each sample performed in duplicate) and expressed as pg/ml±SEM (student t-test).

EXAMPLE 7

Phenotypic Analysis

CD25 and FOXP3 expression by CD3+CD4+ lymphocytes was analyzed using the Beckman Coulter 10-Color Gallios Flow Cytometer and mouse regulatory T Cell Staining Kit with PE Foxp3 FJK-16s, FITC CD4, APC CD25 (eBioscience, San Diego, Calif.) following the manufacturer's instructions.

EXAMPLE 8

Statistics

Statistical analysis was performed using ANOVA and student t test. (Prism 4.0).

EXAMPLE 9

Results

Figure 1:
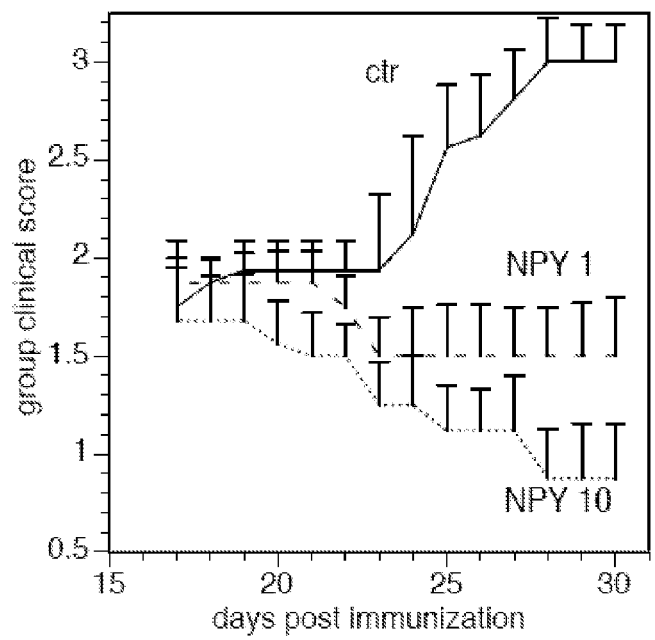
FIG. 1 shows that ingested neuropeptide Y inhibits clinical experimental autoimmune encephalomyelitis attacks. B6 mice (n=8/group) were immunized with MOG peptide 35-55 and were gavaged with 0.1 ml of control saline or 1 mcg or 10 mcg neuropeptide Y as described in methods. Both one and ten mcg ingested neuropeptide Y significantly inhibits clinical experimental autoimmune encephalomyelitis progression compared to control (p<0.001, ANOVA, day 17-30, group clinical score±SEM). The figure shows combined results from 3 separate experiments (total n=24/group).

Experiments determined the immuno-modulatory capability of 1 and 10 mcg ingested (orally administered) neuropeptide Y compared to saline placebo in EAE. Mice were immunized and separated into 3 groups once each mouse attained a clinical score ~1.5-2 (day 17 post immunization) at which time oral dosing was started. The placebo group increased group clinical score from day 17 and plateaued at clinical score=3.0 after 30 days post immunization and 13 days after the initiation of feeding. Active treatment groups fed with 1 and 10 mcg showed significant decreases in group clinical scores after initiation of therapy (day 17) in several experiments ($p<0.001$, ANOVA) with 10 mcg showing the most clinical effect and reduction of disease severity compared to placebo (FIG. 1).

Figure 2:
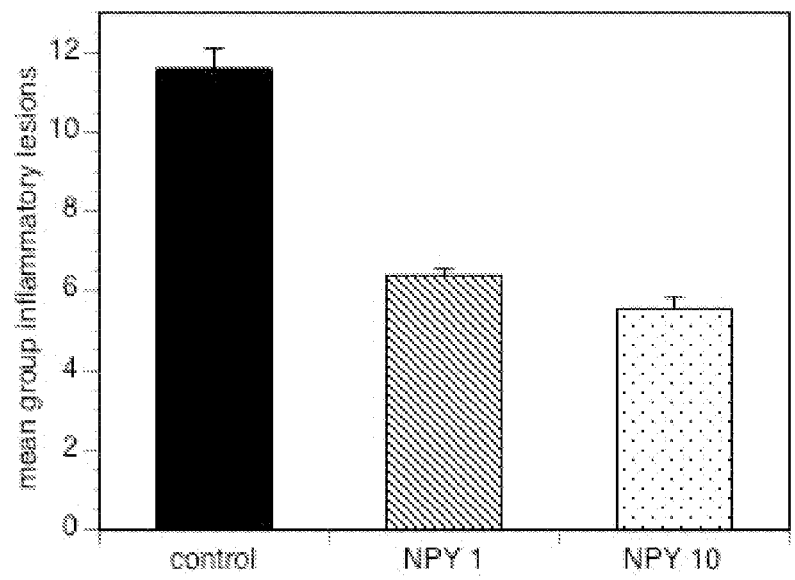
FIG. 2 shows that spinal cords from fed neuropeptide Y mice show significantly less inflammatory foci in the CNS. Spinal cords were harvested as outlined below. There were significantly fewer group mean inflammatory foci in 1 mcg & 10 mcg fed mice compared to placebo fed mice (p<0.008, ANOVA) (n=24/group).

Thirty days following immunization, there were significantly less inflammatory foci in the 1 mcg fed group (mean group inflammatory score=$6.4\pm0.16$, $p<0.008$) and in the 10 mcg fed group (mean group inflammatory score=$5.55\pm0.28$, $p<0.008$) compared to the control mock fed group (mean group inflammatory score=$11.6\pm0.5$) (FIG. 2).

Figure 3:
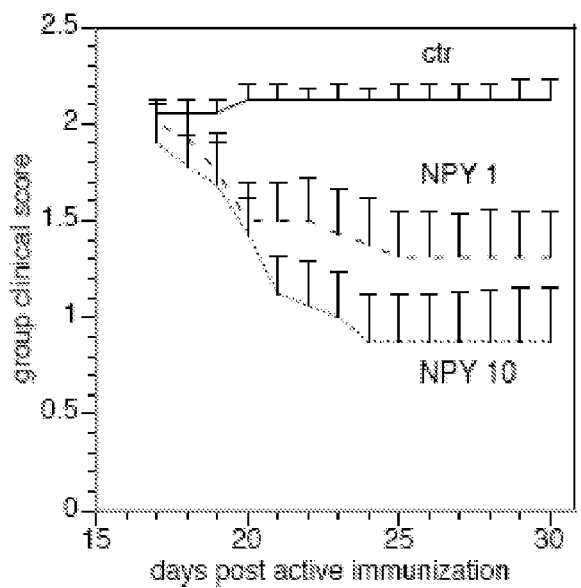
FIG. 3 shows that recipients of adoptively transferred neuropeptide Y fed donor cells protect against active experimental autoimmune encephalomyelitis. Thirty days after inoculation and after peak score of clinical attack, spleens from mock, 1 mcg and 10 mcg neuropeptide Y fed mice were isolated and re-stimulated with MOG peptide 35-55 and adoptively transferred as described below. Recipients of saline fed donor cells increased their group clinical disease severity. In contrast, recipients of neuropeptide Y fed donor cells decreased their group clinical score significantly compared to recipients of saline control cells (p<0.005, days 17-30, group clinical score±SEM). This experiment shows a combination of 3 separate experiments (total n=24/group).

After adoptive transfer of MOG-restimulated splenocytes into actively immunized recipient mice with early clinical disease on day 17 (mean group clinical score ~2.0, respectively), recipients of donor splenocytes from placebo fed mice increased their group clinical disease severity over 13 days to a maximum of 2.3. In contrast, recipients of donor splenocytes from 1 mcg and 10 mcg neuropeptide Y fed mice decreased their group clinical score at day 30 to a score=1.4 and 0.88 respectively (FIG. 3) ($p<0.01$).

Figure 4:
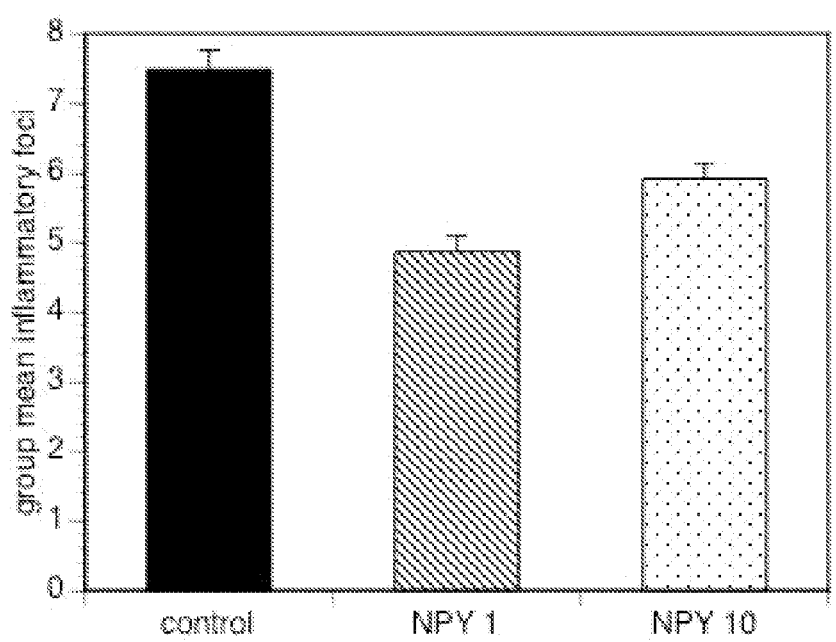
FIG. 4 shows that recipients of adoptively transferred neuropeptide Y fed donor cells show significantly less inflammatory foci compared to control. There were significantly fewer group mean inflammatory foci in recipients of 1 mcg & 10 mcg fed cells compared to recipients of mock fed cells (p<0.008, ANOVA) (n=24/group).

Thirteen days following adoptive transfer, the number of CNS inflammatory foci in the 1 mcg and 10 mcg fed group compared to the control mock placebo group was significantly different (mean group inflammatory score for recipients of placebo fed donors $7.48\pm0.28$) vs recipients of 1 mcg neuropeptide Y fed donors ($4.87\pm0.22$) and 10 mcg neuropeptide Y fed donors ($5.91\pm0.22$, $p<0.001$) (2 way ANOVA, $p<0.001$) (FIG. 4).

Figure 5:
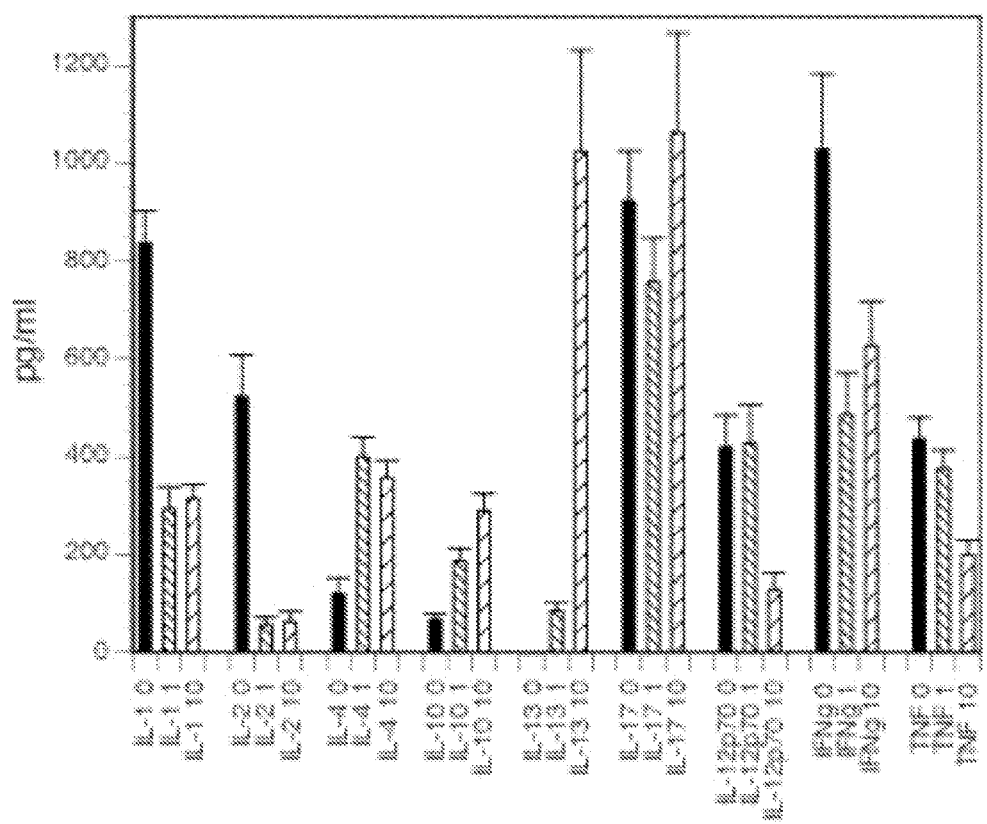
FIG. 5 shows that ingested neuropeptide Y decreases Th1-like cytokines and increases Th2-like cytokines in spleen cells of actively immunized mice. Lymphocytes isolated from spleens from mock fed mice or neuropeptide Y dosed mice were stimulated with MOG peptide 35-55 and measured using an inflammatory cytokine antibody array as described below. Splenic lymphocytes showed decreased levels of IL-1β (p<0.005), Th1-like cytokines IL-2 (p<0.005), IL-12 10 mcg (p<0.01), IFN-γ (p<0.01), TNF-α

The cytokine profiles of MOG re-stimulated spleen and cord lymphocytes were compared in mock dosed versus 1 & 10 mcg neuropeptide Y dosed mice (from FIG. 1). Splenic lymphocytes showed significant decreases in levels of IL-1β, Th1-like cytokines IL-2 and IFN-γ in both neuropeptide Y fed groups compared to the mock fed group (FIG. 5). There was decreased IL-12p70 and TNF-α at 10 mcg neuropeptide Y dosed mice compared to the mock fed group. There was increased peripheral splenic lymphocyte production of MOG induced IL-4, IL-10 and IL-13 in neuropeptide Y dosed vs mock dosed mice (FIG. 5). CNS lymphocytes showed significant decreases in levels of IL-1β, Th1-like cytokines IL-2 and IFN-γ, IL-12, IL-17 ($T_{eff}$) and TNF-α in the neuropeptide Y fed group compared to the mock fed group (FIG. 6). There was increased CNS lymphocyte production of MOG induced IL-13 in neuropeptide Y dosed vs mock dosed mice (FIG. 6).

The cytokine profiles of MOG re-stimulated spleen and cord lymphocytes was also compared in recipients of mock fed, 1 or 10 mcg neuropeptide Y fed donor cells (from FIG. 2). Splenic lymphocytes showed significant decreases in levels of IL-1β, Th1-like cytokines IL-2 10 mcg and IFN-γ, IL-17 ($T_{eff}$), IL-12 and TNF-α in neuropeptide Y fed groups compared to the mock fed group (FIG. 7). There was increased peripheral splenic lymphocyte production of MOG induced IL-13 in neuropeptide Y dosed vs mock dosed mice (FIG. 7). CNS lymphocytes showed significant decreases in levels of IL-1β, IL-17 ($T_{eff}$) in neuropeptide Y fed group compared to the mock fed group (FIG. 8). CNS lymphocytes showed significant decreases in levels of IL-2, IFN-γ and TNF-α in 10 mcg neuropeptide Y fed group compared to the mock fed group (FIG. 8). There was increased CNS lymphocyte production of MOG induced IL-13 in both neuropeptide Y dosed vs mock dosed mice and IL-10 in the 1 mcg neuropeptide Y fed group (FIG. 8).

Whether CD4+CD25+FoxP3+ $T_{reg}$ might be induced by neuropeptide Y feeding was next determined since this might explain protection in actively treated and recipients of adoptively transferred cells from neuropeptide Y fed donors. FACS analysis shows greater than no significant increase in CD4+CD25+FoxP3+ cell frequency in neuropeptide Y fed compared to mock fed mice in actively fed or recipients of actively fed donor cells (data not shown).

Discussion

The present invention shows an overall anti-inflammatory effect of ingested neuropeptide Y in MOG immunized mice. Both 1 mcg and 10 mcg ingested (oral) neuropeptide Y showed significant clinical effect with 10 mg demonstrating the most robust activity. Adoptive transfer of neuropeptide Y fed MOG-re-stimulated splenocytes into recipient mice with early clinical disease suppressed disease compared to splenocytes from mock fed donors. Both active treatment with oral neuropeptide Y or adoptive transfer of splenocytes from neuropeptide Y fed mice showed significantly less CNS inflammation in the neuropeptide Y groups compared to control.

There was a decrease in innate inflammatory cytokines IL-1β and TNF-α, Th1-like cytokines IL-2 and IFN-γ, IL-17 ($T_{eff}$), IL-12p70 as well as increases in Th2-like counter-regulatory cytokines, in particular IL-13. However, there was no increased frequency of Treg cell frequencies in the spleen of neuropeptide Y fed mice compared to controls.

Inoculation of B6 mice with MOG peptides can activate pathogenic neuroantigen-specific Th1 T helper cells in vivo and produce inflammation in murine experimental autoimmune encephalomyelitis (12). IL-17 is produced by Th17 cells distinct from the traditional Th1- and Th2-cell subsets and is involved in generation of autoimmunity (13, 14). IL-12 induces Th1-like cells (15). Th2-like lymphocytes produce IL-4 (16), IL-10 and IL-13 (16) and inhibit experimental autoimmune encephalomyelitis (17). Splenic IL-13 reduces infiltrating mononuclear cells into CNS during experimental autoimmune encephalomyelitis (18).

Previous investigators have shown that parenteral neuropeptide Y significantly inhibits the induction of experimental autoimmune encephalomyelitis by inhibition of MOG 35-55-specific Th1 response in mice (19). Neuropeptide Y can alter Th1 profiles (IL-2 and IFN-γ) in MBP specific T cell lines by increasing IL-4 secretion (20) and inhibiting IFN-γ (21). TNF-α is important in CNS pathology in experimental autoimmune encephalomyelitis (22) and induces experimental autoimmune encephalomyelitis (23). Neuropeptide Y shows a dose-response relationship via specific neuropeptide Y receptors in macrophages (24) and decrease macrophage TNF-α and IL-1β release (25) (26) (27). The present invention demonstrates for the first time that neuropeptide Y by any route can decrease IL-12 and IL-17 and increase IL-13 in vivo.

IL-1β is important in driving IL-17 responses in experimental autoimmune encephalomyelitis (28). Neuropeptide Y decreases IL-1β and LPS induced microglia motility of CD11b-positive cells (25) (29). Neuropeptide Y reduces inflammatory cells accumulation and decreased their adherence and phagocytic capacity via neuropeptide Y Y2/Y5 and Y1/Y2 receptors in vivo and in vitro (25) (30). Such activity may partly explain the decreases in inflammatory foci in treated or recipients of treated donor cells in addition to inhibition of Th17 effector cells.

Neuropeptide Y actions in experimental autoimmune encephalomyelitis may be of particular importance in multiple sclerosis. NK cell function is decreased in MS but neuropeptide Y can increase NK activity in axillary nodes and thymus in mice (31, 32). After i.p. administration, the ratio of myelinated axons to total axons was significantly higher with neuropeptide Y compared to control in developing mouse brains (33). Neuropeptide Y can also inhibit neurogenic inflammation in airways (34). Interestingly, there is less neuropeptide Y in MS CSF compared to control (35).

Preliminary experiments using in vitro neuropeptide Y treated MOG restimulated activated macrophages show robust inhibition of ongoing disease in actively immunized recipients after adoptive transfer. Neuropeptide Y direct activity in macrophages may be responsible for reduction of TNF-α and IL-1β release.

Immunoactive proteins such as SIRS peptide (6), α-MSH (7), (ACTH) (8) and (SST) (9) can all have immunomodulatory activity in experimental autoimmune encephalomyelitis. However, there was no reduction of innate immune cytokines IL-1β or TNF-α in recent experimental autoimmune encephalomyelitis experiments with oral SIRS peptide, α-MSH, ACTH or SST. The present invention shows that a neuropeptide, neuropeptide Y with intrinsic immune activity, can reduce Th1-like activity, induce Th2-like activity and decrease innate immune cytokines without induction of $T_{reg}$ cell. Thus, oral neuropeptide Y shows a unique pattern of immunomodulation for an ingested neuropeptide.

First in human (FIH) trials using oral neuropeptide Y will examine potential toxicity and immunological effects of this novel immunoactive neuroprotein for the potential treatment of autoimmune disease.

The following references were cited herein:
1. Alvord, et al., 1965. *Ann NY Acad Sci* 122:333-345.
2. Raine, et al., 1977. *NY State J Med* 77: 693-1696.
3. Wisnewski, et al., 1977. *Ann Neurol* 1:144-148.
4. Feuer, et al., 1985. *J Neuroimmunol* 10:159-166.
5. Brod, S. A., and D. K. Burns. 1994. *Neurology* 44:1144-1148.
6. Brod, S. A., and Z. Hood. 2007. *J Neuroimmunol* 183:89-95.
7. Brod, S. A., and Z. M. Hood. 2008. *J Neuroimmunol* 193:106-112.
8. Brod, S. A., and Z. Hood. 2011. *Journal of neuroimmunology* 232:131-135.
9. Brod, S. A., and Z. M. Hood. 2011. *Autoimmunity* 44:437-443.
10. Brod, et al., 1995. *J Neuroimmunol* 58:61-69.
11. Brod, et al., 1996. *J Autoimmun* 9:11-20.
12. Tompkins, et al., 2002. *J Immunol* 168:4173-4183.
13. Dong, C. 2006. *Nat Rev Immunol* 6:329-333.
14. Gaffen, et al., 2006. The IL-17 cytokine family. *Vitam Horm* 74:255-282.
15. Eantuzzi, et al., 1997. *European Journal of Immunology* 27:1075-1081.
16. Malefyt, et al., 1991. *J Exp Med* 174:915-924.
17. Monney, et al., 2002. *Nature* 415:536-541.
18. Offner, et al., 2005. *J Immunol* 175:4103-4111.
19. Bedoui, et al., 2003. *J Immunol* 171:3451-3458.
20. Levite, M. 1998. *Proc Natl Acad Sci USA* 95:12544-12549.
21. Kawamura, et al., 1998. *Neuroimmunomodulation* 5:9-15.
22. Renno, et al., 1995. *J Immunol* 154:944-953.
23. Issazadeh, et al., 1995. *J Neurosci Res* 40:579-590.
24. De la Fuente, et al., 1993. *Immunology* 80:259-265.
25. De la Fuente, et al., 2001. *J Neuroimmunol* 116:156-167.
26. Ferreira, et al., 2010. *The Journal of biological chemistry* 285:41921-41934.
27. Wheway, et al., 2005. *J Exp Med* 202:1527-1538.
28. Sutton, et al., 2006. *J Exp Med* 203:1685-1691.
29. Ferreira, et al., 2011. *Journal of neurochemistry*.
30. Mitic, et al., 2011. *Peptides* 32:1626-1633.
31. De la Fuente, et al., 2001. *Regul Pept* 101:73-79.32.
32. Bedoui, et al., 2003. *J Neuroimmunol* 134:1-11.
33. Hashimoto, et al., 2011. *Brain Res* 1373:55-66.
34. Takahashi, et al., 1993. *J Appl Physiol* 75:103-107.
35. Maeda, et al., 1994. *Neuropeptides* 27:323-332.

While the invention has been described with reference to certain embodiments, those skilled in the art will appreciate that modifications may be made without departing from the scope of the invention. All patents and publications cited in this specification are indicative of the level of those skilled in the art to which the invention pertains. All patents and publications herein are incorporated by reference to the same extent as if each publication was specifically indicated as having been incorporated by reference in its entirety.

What is claimed is:

1. A method for decreasing levels of IL-1β, IL-2, IL-12p70, IL-13, IL-12, IL-17 (Teff), TNF-α and IFN-γ and increasing levels of IL-4, IL-10 and IL-13 in a subject, comprising the step of:
  orally administering to the subject an effective dose of neuropeptide Y.

2. The method of claim 1, wherein the neuropeptide Y is administered in a liquid form.

3. The method of claim 1, wherein the neuropeptide Y is administered in a solid form.

4. The method of claim 1, wherein neuropeptide Y is administered in a dose from about 0.1 mcg to about 50 mg.

5. The method of claim 4, wherein neuropeptide Y is administered in a dose from about 1 mg.

6. The method of claim 4, wherein neuropeptide Y is administered in a dose from about 10 mg.

7. The method of claim 1, wherein the subject has multiple sclerosis.

8. The method of claim 1, wherein the subject has rheumatoid arthritis, psoriasis, type 1 diabetes, systemic lupus erythematosus, transplant rejection, autoimmune thyroid disease (Hashimoto's disease), sarcoidosis, scleroderma, granulomatous vasculitis, Crohn's disease, ulcerative colitis, Sjogren's disease, ankylosing spondylitis, polymyositis dermatomyositis, polyarteritis nodosa, immunologically mediated blistering skin diseases, Behcet's syndrome, systemic sclerosis, Goodpasture's disease or immune mediated glomerulonephritis.

9. The method of claim 1, further comprising administering a SIRS peptide.

10. The method of claim 1, further comprising administering a-MSH.

11. The method of claim 1, further comprising administering ACTH.

12. The method of claim 1, further comprising administering SST.

* * * * *